(12) United States Patent
Neathery

(10) Patent No.: US 9,784,650 B1
(45) Date of Patent: Oct. 10, 2017

(54) SEWER GAS SAMPLING AND ANALYZING DEVICES AND METHODS

(71) Applicant: David L. Neathery, Shreveport, LA (US)

(72) Inventor: David L. Neathery, Shreveport, LA (US)

(*) Notice: Subject to any disclaimer, the term of this patent is extended or adjusted under 35 U.S.C. 154(b) by 264 days.

(21) Appl. No.: 14/718,897

(22) Filed: May 21, 2015

(51) Int. Cl.
*E02D 29/14* (2006.01)
*G01N 1/22* (2006.01)

(52) U.S. Cl.
CPC .......... *G01N 1/2226* (2013.01); *E02D 29/14* (2013.01); *G01N 2001/2241* (2013.01)

(58) Field of Classification Search
CPC ............... G01N 1/2226; G01N 1/2205; G01N 2001/2241; E02D 29/14; E02D 29/1436
See application file for complete search history.

(56) References Cited

U.S. PATENT DOCUMENTS

| | | |
|---|---|---|
| 3,048,958 A | 8/1962 | Barnes |
| 3,530,882 A | 9/1970 | Case et al. |
| 3,610,524 A | 10/1971 | Wallen |
| 3,712,009 A | 1/1973 | Campagna |
| 4,285,269 A | 8/1981 | Pelsue et al. |
| 4,373,381 A * | 2/1983 | Kulp .................. E03F 5/02 138/93 |
| 4,512,492 A | 4/1985 | Graybeal |
| 4,586,941 A | 5/1986 | Cooley |
| 4,919,564 A | 4/1990 | Neathery et al. |
| 5,299,327 A | 4/1994 | Wilkerson |
| 5,743,673 A * | 4/1998 | Bravo .................. E02D 29/14 404/25 |
| 5,924,846 A | 7/1999 | Arnold, Jr. et al. |
| 5,966,876 A | 10/1999 | Neathery et al. |
| 6,168,514 B1 | 1/2001 | Weston |
| 6,276,192 B1 | 8/2001 | Sim et al. |
| 6,848,465 B1 | 2/2005 | Ledbetter |
| 6,935,199 B2 * | 8/2005 | Wickland ............. G01N 1/14 73/864.74 |
| 8,237,576 B2 * | 8/2012 | Wander .............. E02D 29/1427 340/632 |
| 8,258,977 B1 * | 9/2012 | Montestruque ....... H01Q 1/225 340/870.02 |
| 8,851,791 B1 | 10/2014 | Putnam |
| 8,926,739 B2 | 1/2015 | Morgan et al. |
| 9,021,619 B2 * | 5/2015 | Paoluccio .............. E03F 5/08 4/220 |
| 2007/0072538 A1 | 3/2007 | Strock |
| 2007/0159326 A1* | 7/2007 | Quist ................... G08B 21/12 340/539.26 |
| 2012/0227168 A1 | 9/2012 | Paoluccio et al. |

(Continued)

*Primary Examiner* — Justin Olamit
(74) *Attorney, Agent, or Firm* — R. Keith Harrison

(57) ABSTRACT

Sewer gas sampling and analyzing devices include a dish-shaped manhole insert having a manhole insert interior and a manhole insert exterior outside the manhole insert interior; a manhole insert vent valve carried by the manhole insert, the manhole insert vent valve having a valve inlet disposed in fluid communication with the manhole insert exterior and a valve outlet and the manhole insert vent valve facilitates substantially unrestricted flow of gas from the valve inlet to the valve outlet; and a gas detector unit disposed in fluid communication with the valve outlet of the manhole insert vent valve. Sewer gas sampling and analyzing methods are also disclosed.

20 Claims, 7 Drawing Sheets

(56) References Cited

U.S. PATENT DOCUMENTS

2013/0051966 A1* 2/2013 Kim .................. H01L 21/67769
　　　　　　　　　　　　　　　　　　414/751.1
2013/0281004 A1　10/2013　Batayneh et al.

* cited by examiner

US 9,784,650 B1

SEWER GAS SAMPLING AND ANALYZING DEVICES AND METHODS

FIELD

Illustrative embodiments of the disclosure generally relate to manholes for sewer systems and the like. More particularly, illustrative embodiments of the disclosure relate to sewer gas sampling and analyzing devices and methods which can be used to sample and analyze sewer conditions such as the composition and quantity of sewer gas emitted through a manhole insert in a manhole structure.

BACKGROUND

The background description provided herein is solely for the purpose of generally presenting the context of various illustrative embodiments of the disclosure. Aspects of the background description are neither expressly nor impliedly admitted as prior art against the claimed subject matter.

In sewer systems, manhole structures typically facilitate access to subterranean piping. A typical manhole structure may be fitted with a manhole cover assembly having a ring-shaped manhole frame which is secured in the above-ground extending portion of the manhole structure. A manhole cover which is seated on the manhole frame can be selectively removed therefrom to facilitate access to the interior of the manhole structure and the sewer system.

One of the problems which is frequently encountered with conventional manhole structures is that methane, hydrogen sulfide, carbon monoxide, sulfur dioxide and other gases have a tendency to accumulate in the sewer system beneath the manhole cover assembly. These gases may create hazardous conditions which may exist with lack of oxygen in some cases to potentially pose a hazard to personnel who must periodically enter the manhole for maintenance, repair, cleaning and/or other purposes.

Accordingly, sewer gas sampling and analyzing devices and methods which can be used to sample and analyze sewer conditions such as the composition and quantity of sewer gas emitted through a manhole insert in a manhole structure are needed.

SUMMARY

Illustrative embodiments of the disclosure are generally directed to sewer gas sampling and analyzing devices which can be used to sample and analyze sewer conditions such as the composition and quantity of sewer gas emitted through a manhole insert in a manhole structure. An illustrative embodiment of the sewer gas sampling and analyzing devices includes a dish-shaped manhole insert having a manhole insert interior and a manhole insert exterior outside the manhole insert interior; a manhole insert vent valve carried by the manhole insert, the manhole insert vent valve having a valve inlet disposed in fluid communication with the manhole insert exterior and a valve outlet and the manhole insert vent valve facilitates substantially unrestricted flow of gas from the valve inlet to the valve outlet; and a gas detector unit disposed in fluid communication with the valve outlet of the manhole insert vent valve.

Illustrative embodiments of the disclosure are further generally directed to sewer gas sampling and analyzing methods. An illustrative embodiment of the sewer gas sampling and analyzing methods includes installing a manhole insert vent valve of a sewer gas sampling and analyzing device in a manhole insert; installing the manhole insert in a manhole over a sewer system; placing a gas detector unit in fluid communication with the manhole insert vent valve; distributing sewer gas from the sewer system through the manhole insert vent valve to the gas detector unit; and obtaining at least one sewer condition reading indicating at least one sewer condition in the sewer system.

BRIEF DESCRIPTION OF THE DRAWINGS

Illustrative embodiments of the disclosure will now be described, by way of example, with reference to the accompanying drawings, wherein:

FIG. 3A is a side view of a manhole insert vent valve seated in a vent plug (illustrated in cross-section) which is inserted in a valve opening in the manhole insert (also in cross-section) of the illustrative sewer gas sampling and analyzing device;

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable users skilled in the art to practice the disclosure and are not intended to limit the scope of the claims. Moreover, the illustrative embodiments described herein are not exhaustive and embodiments or implementations other than those which are described herein and which fall within the scope of the appended claims are possible. Furthermore, there is no intention to be bound by any expressed or implied theory presented in the preceding technical field, background, brief summary or the following detailed description.

Figure 1:
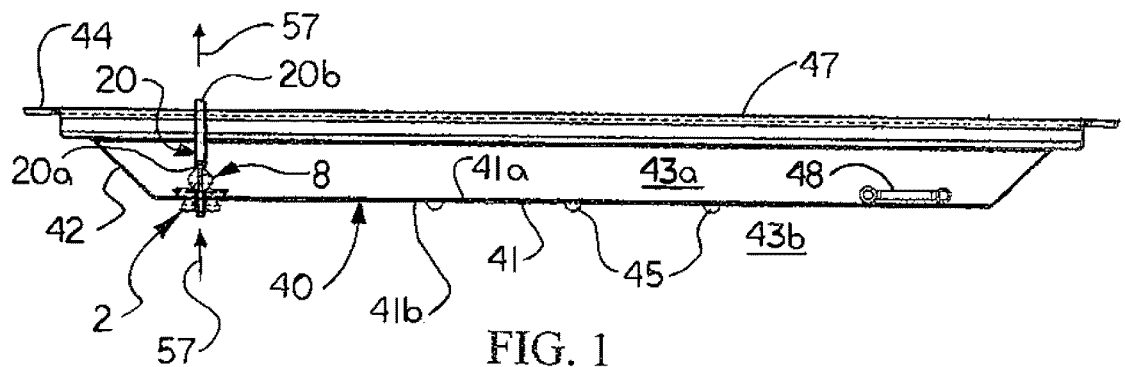
FIG. 1 is a cross-sectional view of manhole insert, manhole insert vent valve and valve tubing components of an illustrative embodiment of the sewer gas sampling and analyzing devices.
Figure 2:
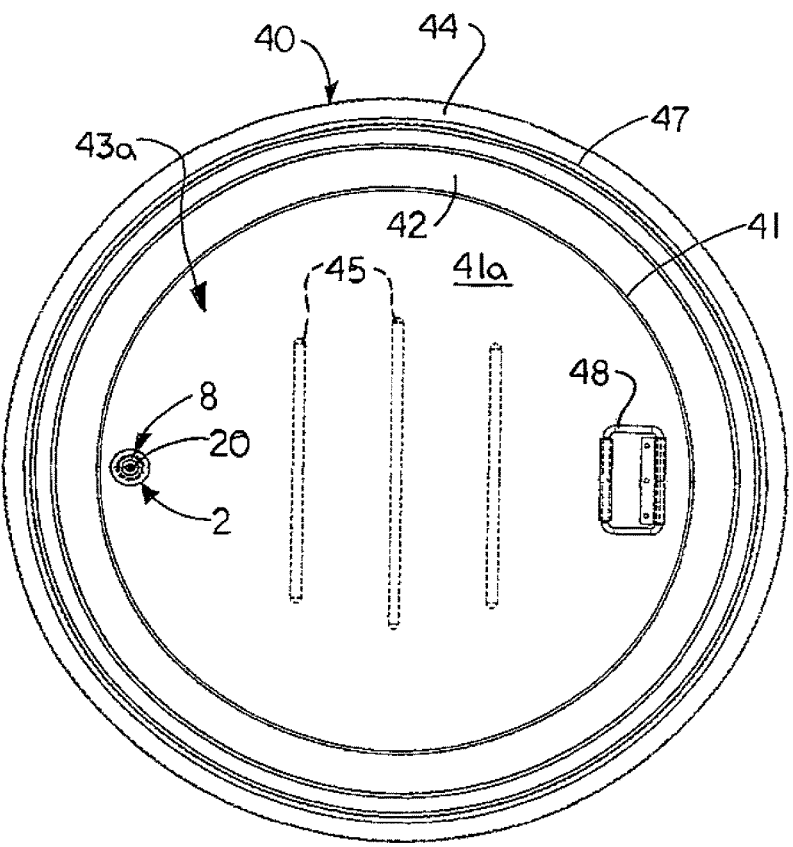
FIG. 2 is a top view of the manhole insert, manhole insert vent valve and valve tubing components of the illustrative sewer gas sampling and analyzing device.
Figure 3:
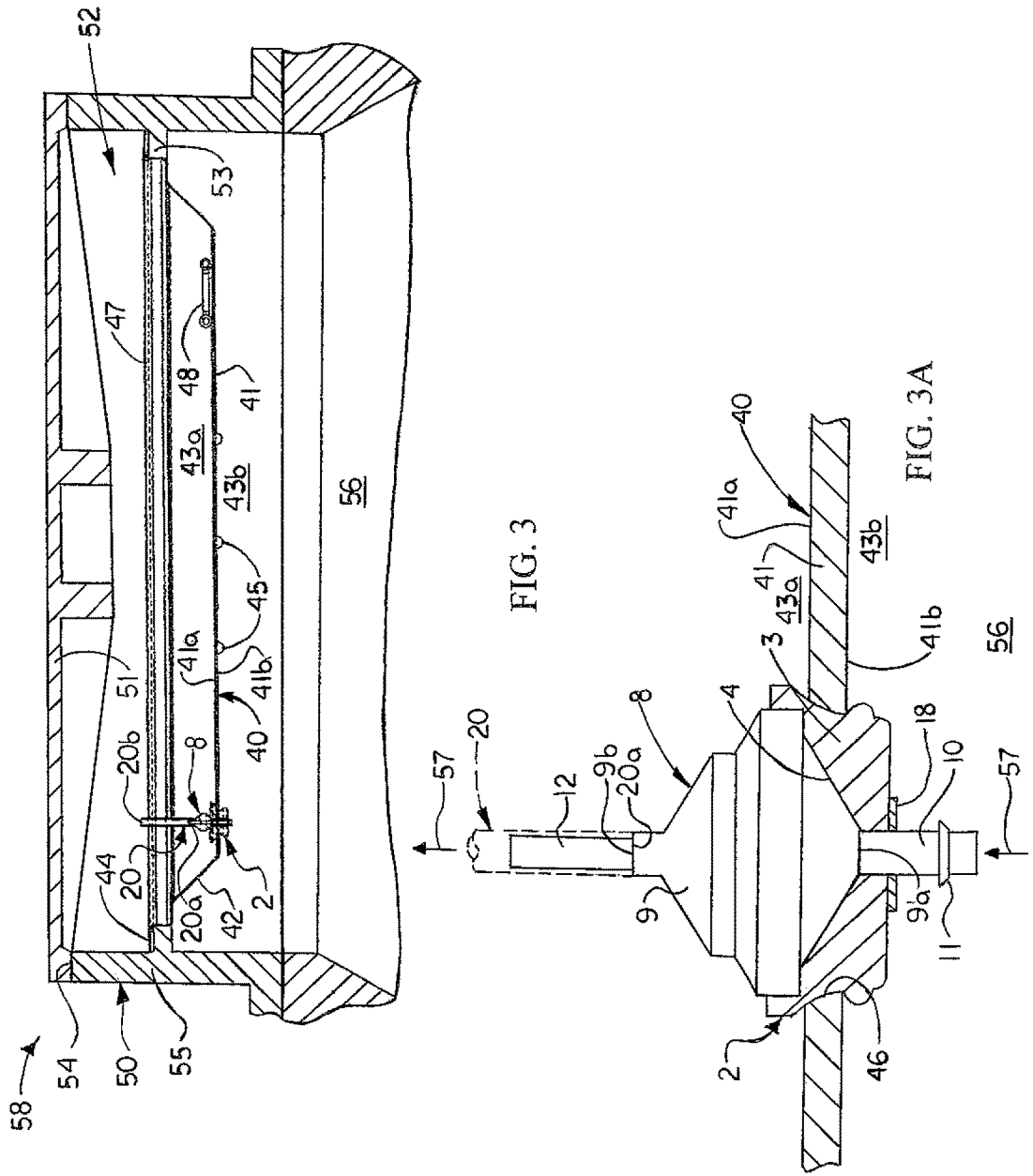
FIG. 3 is a cross-sectional view of the manhole insert, manhole insert vent valve and valve tubing components of the illustrative sewer gas sampling and analyzing device, installed in a manhole structure in typical application of the device.

Referring initially to FIGS. 1-7 of the drawings, an illustrative embodiment of the sewer gas sampling and analyzing devices, hereinafter device, is generally indicated by reference numeral 1 in FIGS. 4-7. As illustrated in FIGS. 1-3A, the device 1 may include a manhole insert 40. As illustrated in FIG. 3, in typical application of the device 1, which will be hereinafter described, the manhole insert 40 may be seated on an annular manhole shoulder 53 inside a manhole frame 55 of a manhole cover assembly 50 in a manhole structure 58. The manhole frame 55 of the manhole cover assembly 50 may be deployed over a subterranean sewer system 56. A manhole cover 51 may normally be supported on an annular manhole cover seat 54 on the manhole frame 55. A manhole opening 52 may be defined between the manhole insert 40 and the manhole cover 51.

As illustrated in FIGS. 1 and 2, in some embodiments, the manhole insert 40 may be pan-shaped with a flat manhole insert bottom 41 and an annular manhole insert side 42 extending outwardly at an angle from the manhole insert bottom 41. The manhole insert bottom 41 and the manhole insert side 42 may define a manhole insert interior 43a. An interior insert bottom surface 41a of the manhole insert bottom 41 may face the manhole insert interior 43a. An exterior insert bottom surface 41b of the manhole insert bottom 41 may face a manhole insert exterior 43b.

The manhole insert side 42 may have a manhole insert rim 47. An annular insert flange 44 may extend outwardly from the manhole insert rim 47 of the manhole insert side 42. Multiple insert stiffeners 45 may be provided in the insert bottom 41 for reinforcement purposes. A valve opening 46 (FIG. 3A) may extend through the manhole insert bottom 41 of the manhole insert 40 for purposes which will be hereinafter described. At least one lift handle 48 may be provided on the interior insert bottom surface 41a of the insert bottom 41 inside the manhole insert interior 43 for the purpose of lifting the manhole insert 40 from the manhole cover assembly 50 to access the underlying sewer system 56.

Figure 4:
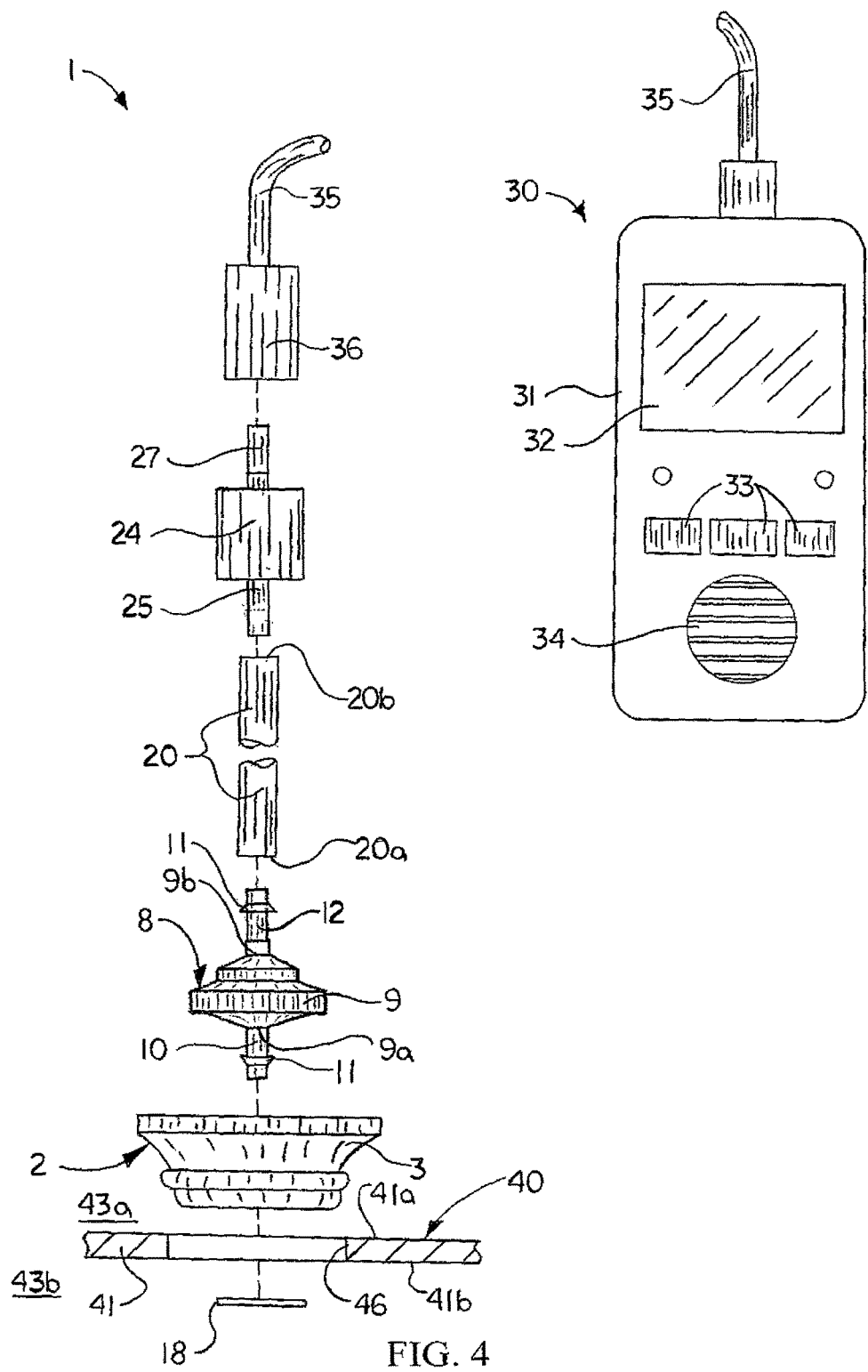
FIG. 4 is an exploded side view, partially in section, of an illustrative sewer gas sampling and analyzing device.
Figure 5:
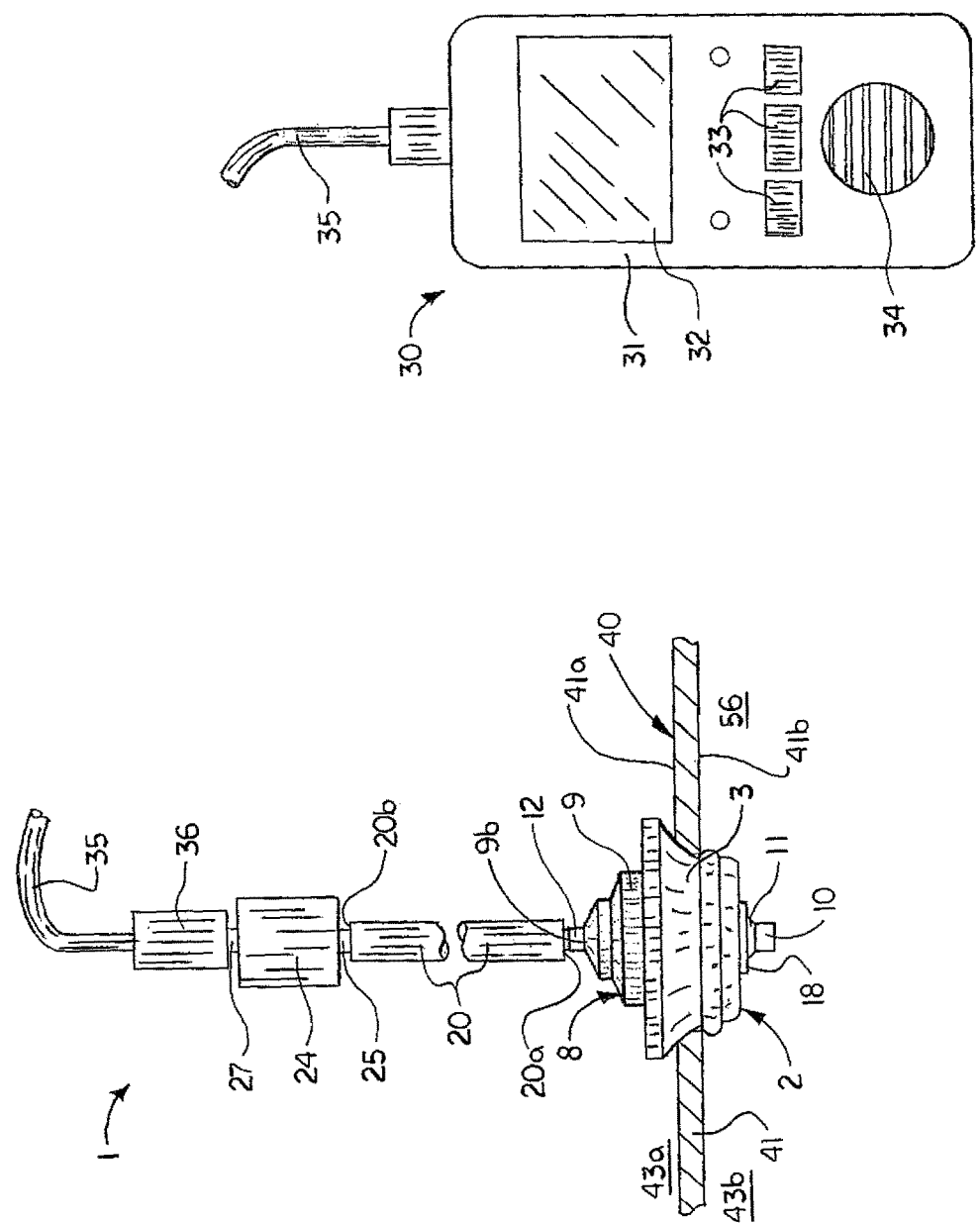
FIG. 5 is a side view, partially in section, of the assembled illustrative sewer gas sampling and analyzing device.
Figure 6:
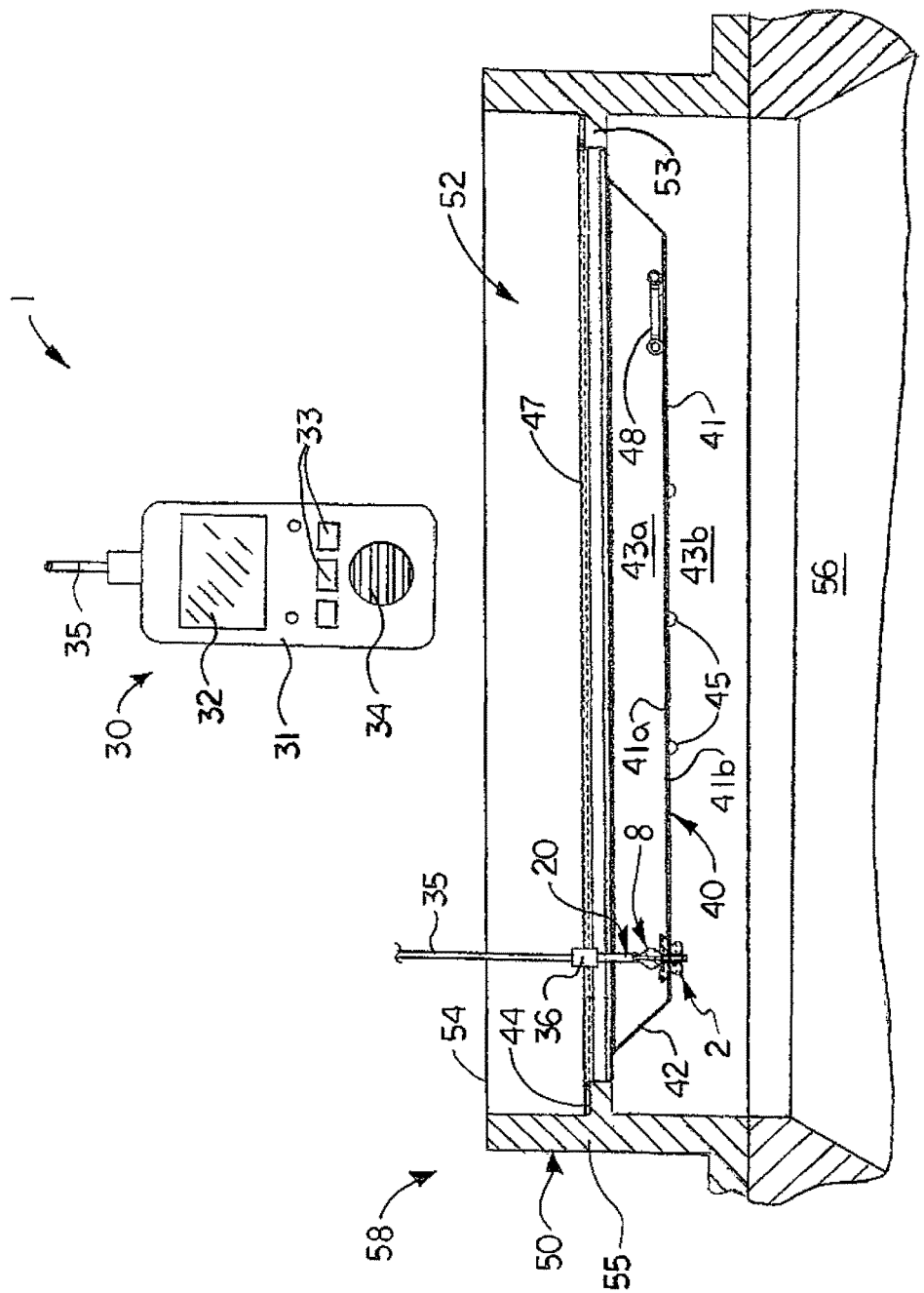
FIG. 6 is a sectional view of a manhole structure with the manhole insert of the illustrative sewer gas sampling and analyzing device inserted in the manhole structure and a gas detector unit coupled to the manhole insert vent valve of the device to sample and analyze sewer gases from a sewer system beneath the manhole structure.
Figure 7:
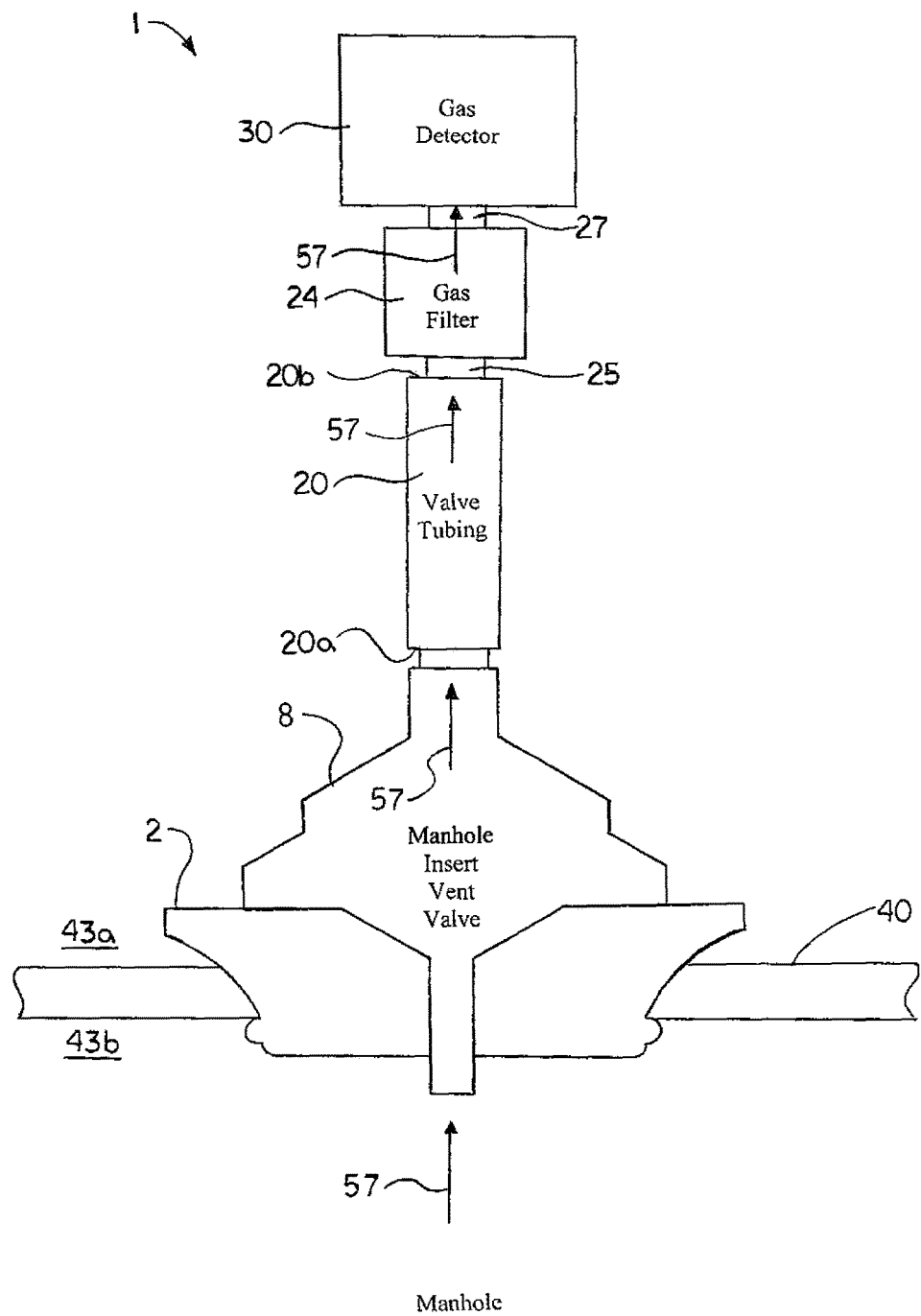
FIG. 7 is a functional block diagram which illustrates typical flow of sewer gas through the manhole insert vent valve, valve tubing and gas filter to the gas detector of an illustrative sewer gas sampling and analyzing device in typical application of the device.

As illustrated in FIGS. 4 and 5, a manhole insert vent valve 8 is seated in the valve opening 46 in the insert bottom 41 of the manhole insert 40 according to the knowledge of those skilled in the art. In some embodiments, a vent plug 2 may be inserted in the valve opening 46. As illustrated in FIG. 3A, the vent plug 2 may include a vent plug wall 3 and a valve seat 4 which extends through the vent plug wall 3. The manhole insert vent valve 8 may be seated in the valve seat 4 of the vent plug 2. In other embodiments, the manhole insert vent valve 8 may be seated in the valve opening 46 using alternative techniques or structures known by those skilled in the art.

The manhole insert vent valve 8 may include any type of valve which is suitable for venting sewer gas 57 from the sewer system 56 beneath the manhole cover assembly 50 and through the insert bottom 41 of the manhole insert 40. In some embodiments, the manhole insert vent valve 8 may include an automotive vacuum valve known by those skilled in the art. For example and without limitation, in some embodiments, the manhole insert vent valve 8 may include a 3/16 inch VITON®/KYNAR® standard check valve (Item No. 64108) which is available from United States Plastic Corp. (www.usplastic.com). As illustrated in FIG. 3A, the manhole insert vent valve 8 may include a valve housing 9 which contains the functional components of the manhole insert vent valve 8. The valve housing 9 may have a valve inlet 9a and a valve outlet 9b. In venting of the sewer gas 57 from the sewer system 56, as further illustrated in FIG. 3A, the manhole insert vent valve 8 may normally facilitate substantially unrestricted flow of sewer gas 57 from the valve inlet 9a through the valve housing 9 to the valve outlet 9b. A valve inlet connector 10 may extend from the valve housing 9 in fluid communication with the valve inlet 9a. A connector barb 11 may be provided on the valve inlet connector 10. A valve outlet connector 12 may extend from the valve housing 9 in fluid communication with the valve outlet 9b. A connector barb 11 may be provided on the valve outlet connector 12. In some embodiments, a retainer washer 18 may be provided on the valve inlet connector 10 to retain the manhole insert vent valve 8 in a seated position in the valve seat 4 of the vent plug 2.

As further illustrated in FIGS. 4-7, valve tubing 20 may be disposed in fluid communication with the valve outlet 9b of the valve housing 9 of the manhole insert vent valve 8. The valve tubing 20 may have a tubing inlet end 20a which is coupled to the valve housing 9 of the manhole insert vent valve 8 at the valve outlet 9b and a tubing discharge end 20b which is opposite the tubing inlet end 20a. The tubing inlet end 20a of the valve tubing 20 may receive the valve outlet connector 12 of the manhole insert vent valve 8. As illustrated in FIG. 1, in some embodiments, the length of the valve tubing 20 may be selected such that the tubing discharge end 20b protrudes beyond the manhole insert rim 47 of the manhole insert 40 for purposes which will be hereinafter described.

As illustrated in FIGS. 4 and 5, a gas filter 24 may be disposed in fluid communication with the valve outlet 9b of the valve housing 9 of the manhole insert vent valve 8. The gas filter 24 may filter moisture and/or particulate impurities from the sewer gas 57 as the sewer gas 57 flows through the gas filter 24. In some embodiments, the gas filter 24 may be disposed in fluid communication with the tubing discharge end 20b of the valve tubing 20, as illustrated. In some embodiments, a filter inlet connector 25 may extend from a first end of the gas filter 24 for insertion into the tubing discharge end 20b of the valve tubing 20. A filter outlet connector 27 may extend from a second end of the gas filter 24. In other embodiments, the gas filter 24 may be omitted from the device 1.

A gas detector unit 30 may be disposed in fluid communication with the valve outlet 9b of the valve housing 9 of the manhole insert valve 8. In some embodiments, the gas detector unit 30 may be disposed in fluid communication with the gas filter 24 and may be selectively coupled to the filter outlet connector 27, as illustrated. The gas detector unit 30 may include any type of commercially-available electronic gas detector unit which is capable of detecting and monitoring or analyzing the oxygen content and the presence and quantities of toxic or flammable gases such as methane, hydrogen sulfide, carbon monoxide, sulfur dioxide and/or other potentially hazardous gases. In some embodiments, the gas detector unit 30 may include a hand-held gas detector unit console 31. A display 32 may be provided on the gas detector unit console 31. Controls 33 on the gas detector unit console 31 may facilitate selection from among multiple display parameters which appear on the display 32. A speaker 34 may be provided on the gas detector unit console 31 to provide an audible indication of potentially hazardous gases detected using the gas detector unit 30. An elongated detector tube 35 may extend from the gas detector unit console 31. In some embodiments, a tube connector 36 may terminate the detector tube 35. The tube connector 36 may be adapted for connection to the filter outlet connector 27 on the gas filter 24. A non-limiting example of a gas detector unit 30 which is suitable for implementation of the device 1 is the Tetra Multi-Gas Monitor which is available from Crowcon Detection Instruments Ltd. (www.crowcon.com). In some embodiments, the gas filter 24 may be a component part of the gas detector unit 30. A gas pump (not illustrated) may be incorporated into the gas detector unit 30 according to the knowledge of those skilled in the art in some embodiments. Accordingly, in typical application of the device 1, which will be hereinafter described, the gas pump (not illustrated) in the gas detector unit 30 may be operable to pump the sewer gas 57 from the sewer system 56 through the manhole insert vent valve 8 and the valve tubing 20, through the gas filter 24 to the gas detector unit 30. The gas filter 24 may remove moisture and/or particulate impurities from the sewer gas 57. In some applications, the sewer gas 57 may flow from the sewer system 56 to the gas detector unit 30 of the device 1 under natural pressure and without operation of a gas pump. The gas detector unit 30 analyzes the sampled sewer gas 57 and indicates at least one sewer condition such as the quantities and compositions of gases in the sewer gas 57 and the quantity of oxygen in the sewer system 56. This discretionary information may enable personnel to take precautionary measures in removing the manhole insert 40 from the manhole cover assembly 50 preparatory to entering the sewer system 56 through the manhole structure 58.

As illustrated in FIGS. 3, 3A, 6 and 7, typical application of the device 1 may be as follows. The manhole insert 40, with the vent plug 2, the manhole insert vent valve 8 and the valve tubing 20 installed therein, is seated in the manhole 50 over the sewer system 56 typically by initially removing the manhole cover 51 from the annular manhole over seat 54 on the manhole frame 55, seating the manhole insert flange 44 of the manhole insert 40 onto the annular manhole shoulder 53 in the manhole frame 55 and replacing the manhole cover 51 on the manhole cover seat 54. Accordingly, the manhole insert interior 43a of the manhole insert 40 communicates with the manhole opening 52 beneath the manhole cover 51, whereas the manhole insert exterior 43b of the manhole insert 40 communicates with the underlying sewer system 56. The valve inlet connector 10 on the valve housing 9 of the manhole insert vent valve 8 is disposed in fluid communication with the manhole insert exterior 43b of the manhole insert 40. The manhole insert vent valve 8 normally facilitates substantially unrestricted unidirectional flow of sewer gas 57 from the sewer system 56 through the valve vent connector 10, the valve housing 9 and the valve outlet connector 12, respectively, of the manhole insert vent valve 8, and the valve tubing 20. The sewer gas 57 may be discharged from the tubing discharge end 20b of the valve tubing 20 and accumulate in the manhole opening 52 beneath the manhole cover 51, or alternatively, may be vented from the manhole opening 52 through one or more manhole cover openings (not illustrated) in the manhole cover 51.

When repair, maintenance and/or cleaning of the sewer system 56 beneath the manhole structure 58 is required, the manhole cover 51 may be removed from the manhole cover seat 54, exposing the upward-standing valve tubing 20 of the device 1. As illustrated in FIGS. 4 and 5, the detector tube 35 of the gas detector unit 30 may be connected to the gas filter 24, and the gas filter 24 may be connected to the valve tubing 20. In some embodiments, the gas pump (not illustrated) may be operated to pump the sewer gas 57 from the sewer system 56 and through the valve inlet connector 10, the valve housing 9 and the valve outlet connector 12, respectively, of the manhole insert vent valve 8 and then through the valve tubing 20 and the detector tube 35 to the gas detector unit 30. In some applications, the sewer gas 57 may flow from the sewer system 56 to the gas detector unit 30 of the device 1 under natural pressure and without operation of the gas pump. The gas filter 24 may remove moisture and/or particulate impurities from the sewer gas 57. Accordingly, the gas detector unit 30 may detect and analyze the sewer gas 57 and, based on analysis of the sewer gas 57, display one or more sewer condition readings which indicate sewer conditions that may potentially adversely affect personnel who take part in the repair, maintenance and/or cleaning operation in the sewer system 56. These sewer condition readings may include such parameters as the noxious gaseous constituents of the sewer gas 57 as well as the concentrations of the constituents and quantification of oxygen in the sewer gas 57. These parameters are known by or can be readily determined by personnel who are routinely employed in the repair, maintenance and/or cleaning of sewer systems 56.

After the sewer condition readings are taken, the gas filter 24 may be disconnected from the valve tubing 20. In the event that the sewer condition readings indicated by the gas detector unit 30 reveal that concentrations of the gaseous constituents in the sewer gas 57 are above a predetermined minimum concentration threshold level for the constituents and/or the oxygen content of the sewer gas 57 falls below a predetermined minimum oxygen content threshold level, the personnel may take precautionary measures upon subsequently removing the manhole insert 40 from the manhole structure 58 to prevent the noxious constituents and/or lack of oxygen in the sewer gas 57 from rendering any of the personnel unconscious. These precautions may prevent the personnel from subsequently inadvertently falling into the sewer system 56. Corrective measures such as the installation of blowers (not illustrated) in the sewer system 56 may subsequently be undertaken to more effectively introduce fresh air into the sewer system 56. After the repair, maintenance and/or cleaning operation is completed, the manhole insert 40 may be replaced on the manhole shoulder 53 and the manhole cover 51 replaced on the manhole cover seat 54 with the vent plug 2, the manhole insert vent valve 8 and the valve tubing 20 remaining in place in the manhole insert 40.

As illustrated in FIG. 3, it will be appreciated by those skilled in the art that in some embodiments of the sewer gas sampling and analyzing device 1, the length of the valve tubing 20 may be selected such that the tubing discharge end 20b of the valve tubing 20 protrudes beyond the manhole insert rim 47 of the manhole insert 40. Accordingly, the valve tubing 20 prevents rainwater or other precipitation which may accumulate in the manhole insert interior 43a of the manhole insert 40 from entering the manhole insert vent valve 8 through the valve outlet 9b.

Figure 8:
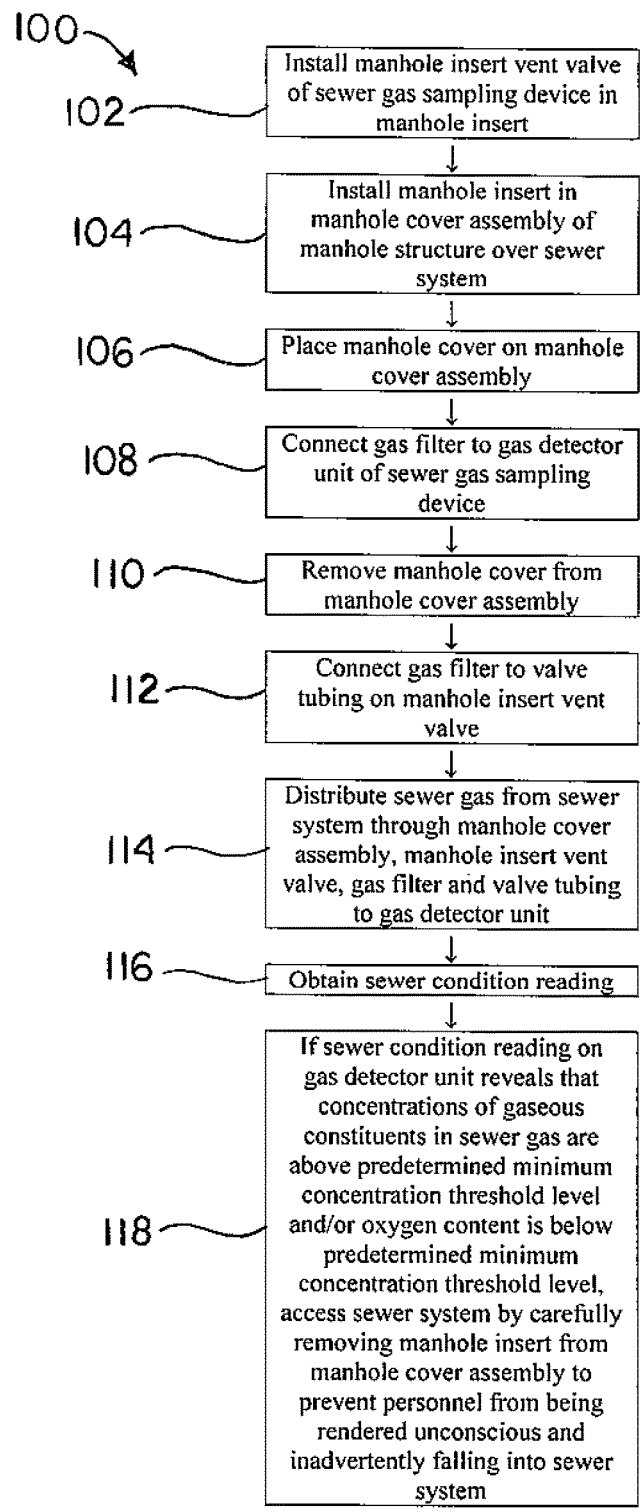
FIG. 8 is a flow diagram of an illustrative embodiment of the sewer gas sampling and analyzing methods.

Referring next to FIG. 8 of the drawings, a sewer gas sampling and analyzing method 100 is illustrated. At block 102, a manhole insert vent valve of a sewer gas sampling and analyzing device is installed in a manhole insert. At block 104, the manhole insert is installed in a manhole cover assembly of a manhole structure over a sewer system. At block 106, a manhole cover is placed on the manhole cover assembly. At block 108, a gas filter may be connected to a gas detector unit of the sewer gas sampling and analyzing device. At block 110, the manhole cover is removed from the manhole cover assembly. At block 112, the gas filter is connected to valve tubing on the manhole insert vent valve. At block 114, sewer gas may be pumped from the sewer system through the manhole cover assembly, the manhole insert vent valve and the valve tubing to the gas detector unit. In other embodiments, the sewer gas may flow from the sewer system through the manhole cover assembly, the manhole insert vent valve and the valve tubing to the gas detector unit under natural pressure and without operation of a gas pump.

At block 116, at least one sewer condition reading is obtained. The sewer condition reading may include such parameters as the noxious gaseous constituents of the sewer gas as well as the concentrations of the constituents and quantification of oxygen in the sewer gas. At block 118, the manhole insert may be carefully removed from the manhole cover assembly to prevent personnel from being rendered unconscious and inadvertently falling into the sewer system if the sewer condition reading on the gas detector unit reveals concentrations of the gaseous constituents in the sewer gas that are above a predetermined minimum concentration threshold level for the constituents and/or an oxygen content which falls below a predetermined minimum oxygen content threshold level.

While illustrative embodiments of the disclosure have been described above, it will be recognized and understood that various modifications can be made and the appended claims are intended to cover all such modifications which may fall within the spirit and scope of the disclosure.

What is claimed is:

1. A sewer gas sampling and analyzing device, comprising:
    a dish-shaped manhole insert having a manhole insert bottom with an interior insert bottom surface and an exterior insert bottom surface, a manhole insert interior at the interior insert bottom surface of the manhole insert bottom and a manhole insert exterior outside the manhole insert interior at the exterior insert bottom surface of the manhole insert bottom;
    a manhole insert vent valve carried by the manhole insert, the manhole insert vent valve having a valve inlet disposed in fluid communication with the manhole insert exterior and a valve outlet, the valve inlet disposed on an exterior insert bottom surface side of the manhole insert bottom, the manhole insert vent valve facilitating substantially unrestricted flow of gas from the valve inlet to the valve outlet; and
    a gas detector unit disposed in fluid communication with the valve outlet of the manhole insert vent valve.

2. The sewer gas sampling and analyzing device of claim 1 further comprising a valve opening in the manhole insert and a vent plug seated in the valve opening, and wherein the manhole insert vent valve is seated in the vent plug.

3. A sewer gas sampling and analyzing device, comprising:
    a dish-shaped manhole insert having a manhole insert interior and a manhole insert exterior outside the manhole insert interior;
    a manhole insert vent valve carried by the manhole insert, the manhole insert vent valve having a valve inlet disposed in fluid communication with the manhole insert exterior and a valve outlet and the manhole insert vent valve facilitates substantially unrestricted flow of gas from the valve inlet to the valve outlet;
    a gas detector unit disposed in fluid communication with the valve outlet of the manhole insert vent valve; and
    wherein the manhole insert vent valve comprises a vacuum valve.

4. The sewer gas sampling and analyzing device of claim 1 wherein the manhole insert vent valve comprises a valve housing, a valve inlet connector disposed in fluid communication with the valve inlet and extending from the valve housing and a valve outlet connector disposed in fluid communication with the valve outlet and extending from the valve housing opposite the valve inlet connector, and wherein the valve inlet connector is disposed in fluid communication with the manhole insert exterior and the gas detector unit is disposed in fluid communication with the valve outlet connector.

5. A sewer gas sampling and analyzing device, comprising:
    a dish-shaped manhole insert having a manhole insert interior and a manhole insert exterior outside the manhole insert interior;
    a manhole insert vent valve carried by the manhole insert, the manhole insert vent valve having a valve inlet disposed in fluid communication with the manhole insert exterior and a valve outlet and the manhole insert vent valve facilitates substantially unrestricted flow of gas from the valve inlet to the valve outlet; d
    a gas detector unit disposed in fluid communication with the valve outlet of the manhole insert vent valve; and
    wherein the manhole insert comprises a flat manhole insert bottom and an annular manhole insert side extending outwardly at an angle from the manhole insert bottom, and wherein the manhole insert vent valve is carried by the manhole insert bottom.

6. The sewer gas sampling and analyzing device of claim 1 further comprising a valve tubing disposed in fluid communication with the valve outlet of the manhole insert vent valve, and wherein the gas detector unit is disposed in fluid communication with the valve tubing.

7. The sewer gas sampling and analyzing device of claim 6 wherein the manhole insert comprises a manhole insert rim and the valve tubing comprises a tubing inlet end disposed in fluid communication with the valve outlet of the manhole insert vent valve and a tubing discharge end opposite the tubing inlet end, the tubing discharge end extending beyond the manhole insert rim of the manhole insert.

8. The sewer gas sampling and analyzing device of claim 6 wherein the manhole insert vent valve comprises a valve housing, a valve inlet connector disposed in fluid communication with the valve inlet and extending from the valve housing and a valve outlet connector disposed in fluid communication with the valve outlet and extending from the valve housing opposite the valve inlet connector, and the valve tubing is coupled to the valve outlet connector, and wherein the valve inlet connector is disposed in fluid communication with the manhole insert exterior.

9. A sewer gas sampling and analyzing device, comprising:
    a dish-shaped manhole insert having a manhole insert bottom with an exterior insert bottom surface facing a manhole insert exterior and an interior insert bottom surface facing a manhole insert interior, an insert side extending from the manhole insert bottom and a manhole insert flange extending outwardly from the manhole insert side;
    a manhole insert vent valve carried by the manhole insert, the manhole insert vent valve having a valve inlet disposed in fluid communication with the manhole insert exterior and a valve outlet, the valve inlet disposed on an exterior insert bottom surface side of the manhole insert bottom, the manhole insert vent valve facilitating substantially unrestricted flow of gas from the valve inlet to the valve outlet;
    a gas filter disposed in fluid communication with the valve outlet of the manhole insert vent valve; and
    a gas detector unit disposed in fluid communication with the gas filter.

10. The sewer gas sampling and analyzing device of claim 9 further comprising a valve opening in the manhole insert bottom of the manhole insert and a vent plug seated in the valve opening, and wherein the manhole insert vent valve is seated in the vent plug.

11. A sewer gas sampling and analyzing device, comprising:
- a dish-shaped manhole insert having a manhole insert bottom with an exterior insert bottom surface facing a manhole insert exterior and an interior insert bottom surface facing a manhole insert interior, an insert side extending from the manhole insert bottom and a manhole insert flange extending outwardly from the manhole insert side;
- a manhole insert vent valve carried by the manhole insert, the manhole insert vent valve having a valve inlet disposed in fluid communication with the manhole insert exterior and a valve outlet and the manhole insert vent valve facilitates substantially unrestricted flow of gas from the valve inlet to the valve outlet;
- a gas filter disposed in fluid communication with the valve outlet of the manhole insert vent valve; and
- a gas detector unit disposed in fluid communication with the gas filter; and
- wherein the manhole insert vent valve comprises a vacuum valve.

12. The sewer gas sampling and analyzing device of claim 9 wherein the manhole insert vent valve comprises a valve housing, a valve inlet connector disposed in fluid communication with the valve inlet and extending from the valve housing and a valve outlet connector disposed in fluid communication with the valve outlet and extending from the valve housing opposite the valve inlet connector, and wherein the valve inlet connector is disposed in fluid communication with the manhole insert exterior and the gas detector unit is disposed in fluid communication with the valve outlet connector.

13. The sewer gas sampling and analyzing device of claim 9 further comprising a valve tubing disposed in fluid communication with the valve outlet of the manhole insert vent valve, and wherein the gas detector unit is disposed in fluid communication with the valve tubing.

14. The sewer gas sampling and analyzing device of claim 13 wherein the manhole insert comprises a manhole insert rim and the valve tubing comprises a tubing inlet end disposed in fluid communication with the valve outlet of the manhole insert vent valve and a tubing discharge end opposite the tubing inlet end, the tubing discharge end extending beyond the manhole insert rim of the manhole insert.

15. A sewer gas sampling and analyzing method, comprising:
- installing a manhole insert vent valve of a sewer gas sampling and analyzing device in a manhole insert;
- installing the manhole insert in a manhole over a sewer system;
- placing a gas detector unit in fluid communication with the manhole insert vent valve;
- distributing sewer gas from the sewer system through the manhole insert vent valve to the gas detector unit; and
- obtaining at least one sewer condition reading indicating at least one sewer condition in the sewer system.

16. The sewer gas sampling and analyzing method of claim 15 wherein obtaining at least one sewer condition reading comprises pumping the sewer gas from the sewer system through the manhole insert vent valve to the gas detector unit.

17. The sewer gas sampling and analyzing method of claim 16 wherein placing a gas detector unit in fluid communication with the manhole insert vent valve comprises connecting a gas filter to the gas detector unit and the manhole insert vent valve, respectively, and filtering the sewer gas from the manhole insert vent valve.

18. The sewer gas sampling and analyzing method of claim 15 wherein placing a gas detector unit in fluid communication with the manhole insert vent valve comprises placing a valve tubing in fluid communication with the manhole insert vent valve and placing the gas detector unit in fluid communication with the valve tubing.

19. The sewer gas sampling and analyzing method of claim 18 wherein obtaining at least one sewer condition reading comprises pumping the sewer gas from the sewer system through the manhole insert vent valve and the valve tubing to the gas detector unit.

20. The sewer gas sampling and analyzing method of claim 19 wherein placing a gas detector unit in fluid communication with the manhole insert vent valve comprises connecting a gas filter to the gas detector unit and the valve tubing, respectively, and filtering the sewer gas from the manhole insert vent valve.

* * * * *